United States Patent [19]

Abbott et al.

[11] 4,378,500

[45] Mar. 29, 1983

[54] FLUORESCENCE ENHANCEMENT OF DANSYL DERIVATIVES

[75] Inventors: Seth R. Abbott, Concord; Robert Cunico, Pleasant Hill, both of Calif.

[73] Assignee: Varian Associates, Inc., Palo Alto, Calif.

[21] Appl. No.: 242,194

[22] Filed: Mar. 10, 1981

[51] Int. Cl.³ ............................................. G01N 21/34
[52] U.S. Cl. .................................. 250/304; 250/461.2
[58] Field of Search ............... 250/304, 461 R, 432 R, 250/436; 23/230 R

[56] References Cited

U.S. PATENT DOCUMENTS

| | | | |
|---|---|---|---|
| 3,303,043 | 2/1967 | Halpaap et al. | 250/304 |
| 3,814,939 | 6/1974 | Parker et al. | 250/304 |
| 4,181,853 | 1/1980 | Abu-Shumays et al. | 250/304 |
| 4,233,030 | 11/1980 | Twitchett et al. | 250/461 R |

*Primary Examiner*—Bruce C. Anderson
*Attorney, Agent, or Firm*—Stanley Z. Cole; Norman E. Reitz; Pauline A. Clarke

[57] ABSTRACT

A method for fluorescence enhancement of dansyl derivatives of active hydrogen compounds which are easily separated in a liquid chromatography column using a polar solvent system but whose fluorescence efficiency is diminished in such polar solvents, by changing the environment of the dansyl derivative without changing the solvent.

28 Claims, No Drawings

FLUORESCENCE ENHANCEMENT OF DANSYL DERIVATIVES

DESCRIPTION

1. Technical Field

This invention relates to a novel method for fluorescence enhancement of dansylated derivatives eluted from a liquid chromatography column, and, more specifically, to a method for enhancing fluorescence by changing the environment of the dansylated derivatives without changing the solvent.

2. Background Art

For many years one of the aims of liquid chromatography and especially HPLC has been the identification and/or quantitation of small amounts of compounds as they are eluted from the chromatography column without further separation or manipulation steps. Recently, this has been especially true of biologically important compounds, many of which contain an active hydrogen site. Such compounds are normally isolated as mixtures in small quantities. Because of the active hydrogen, these compounds are readily converted to derivatives to enhance detectability.

Dansyl derivatives of active hydrogen compounds such as phenols, amines and amino acids are known. Fluorescence detection of these derivatives after liquid chromatography, can be accomplished using either polar or non-polar solvent systems. However, the sample quantity necessary for detection varies with the solvent. In non-polar solvent systems, the fluorescence of these dansyl derivatives is high but the separation is often poor. When polar solvent systems are used for gradient elution, separation is good. However, fluorescence response is low and non-uniform, that is, the fluorescence efficiency changes with a change in solvent polarity. In the prior art, either separation or fluorescence efficiency is sacrificed to detect dansyl derivatives of active hydrogen compounds.

Another prior art method to increase fluorescence of dansyl derivatives of active hydrogen compounds eluted from chromatography columns, has been to achieve separation using a polar solvent system and then evaporate or otherwise remove the polar solvent and replace it with a non-polar solvent. There is, however, a likelihood of sample loss during solvent removal, especially when dealing with small sample quantities, and an increased analysis time required for solvent removal.

Packed flow cells have been used in the prior art. In U.S. Pat. No. 4,181,853, assigned to the same assignee as the present invention, a flow cell packed with aflatoxin-adsorbing particles such as silica, alumina, a bonded phase or an ion exchange resin, was used to increase the fluorescence of aflatoxins eluted from a non-polar column in non-polar solvents. Lloyd [The Analyst, 100(1193), 529(1975)] used a flow cell packed with silica to detect the fluorescence of polynuclear aromatic hydrocarbons. However, neither of these documents discusses the fluorescence enhancement of dansyl derivatives eluted in a polar solvent by using a flow cell packed with a non-polar packing, that is, a change in the sample environment without changing the solvent.

DISCLOSURE OF THE INVENTION

It is accordingly one object of the present invention to provide a novel method for fluorescence enhancement of mixtures of dansyl derivatives of active hydrogen compounds which are easily separated in a liquid chromatography column using a polar solvent system but whose fluorescence efficiency is diminished in such polar solvents.

A further object is to provide such an automatic method for fluorescence enchancement by changing the environment of dansyl derivatives of active hydrogen compounds as they are eluted in polar solvent systems without changing the solvent system.

An even further object is to provide a fluorescence enhancement method in which the polar eluant containing dansyl derivatives of active hydrogen compounds is passed through a cell packed with a non-polar packing material in such a way that there is caused a dynamic equilibrium of the dansyl derivative of the active hydrogen compound between the polar solvent system and the non-polar packing material.

A further object is to provide a method for fluorescence enhancement in which the polar eluant contains dansyl derivatives of active hydrogen compounds whose fluorescences are enhanced in non-polar solvents and impurities or contaminants which cannot be completely separated by liquid chromatography but whose fluorescence is quenched in non-polar solvents. This method includes passing the polar eluant containing a dansyl derivative and an impurity or contaminant through a flow cell packed with a non-polar packing material in such a way that there is caused a dynamic equilibrium of the dansyl derivative of the active hydrogen compound and impurity or contaminant between the polar solvent system and the non-polar packing material. The fluorescence of the dansyl derivative of the active hydrogen compound is enhanced and the fluorescence of the impurity or contaminant is diminished.

It is an even further object to provide a method for fluorescence enhancement of dansyl derivatives of active hydrogen compounds which enables good separation of the dansyl derivatives while enabling increased sensitivity, thereby allowing the detection of small quantities of dansyl derivatives of active hydrogen compounds.

Other objects and advantages of the present invention will become apparent as the description thereof proceeds.

In satisfaction of the foregoing objects and advantages, there is provided by the present invention a method for enhancing the fluorescence of dansyl derivatives of active hydrogen compounds which changes the environment of the dansyl derivative without changing the solvent. The method includes the first essential step of passing the polar dansyl derivative-containing eluant eluted from a non-polar chromatography column through a flow cell packed with a non-polar packing material whereby there is caused a dynamic equilibrium of the dansyl derivative compound between the polar solvent and the non-polar packing material. The packed flow cell is irradiated with electromagnetic radiation of a frequency that causes the dansyl derivative to fluoresce in the non-polar environment and the fluorescence of the dansyl derivative is detected.

In addition, there is provided by the present invention a method for enhancing the fluorescence of dansyl derivatives of active hydrogen compounds which cannot be completely separated by liquid chromatography using polar solvent systems, but whose impurity or contaminant has a fluorescence which is quenched in non-polar environments while the fluorescence of the dansyl derivative is enhanced in non-polar environments. The method includes the first step of passing the mixture eluted from a non-polar chromatography column in a polar solvent through a cell packed with a non-polar packing material in such a way that there is caused a dynamic equilibrium of the dansyl derivative and the contaminant between the polar solvent system and the non-polar cell packing material, thereby causing a change in sample environment without changing solvent. The packed flow cell is irradiated with electromagnetic radiation of a frequency that causes the dansyl derivative to fluoresce in the non-polar environment and the impurity or contaminant to be quenched, and the fluorescence of the dansyl derivative is detected.

BEST MODE FOR CARRYING OUT THE INVENTION

As indicated above, the present invention is concerned with a method for enhancing the fluorescence detection of dansyl derivatives which have been separated using a polar solvent system. For good separation of mixtures of dansyl derivatives of active hydrogen compounds, non-polar column packings such as microparticulate silica bonded to, for example, hydrocarbons of carbon chain length 2–22, phenyl, diphenyl, phenylethyl or alkylcyano are advantageously used. A hydrocarbon of carbon chain length 16–20 is preferred. These column packing materials are available commercially as, for example, LiChrosorb RP-8 or RP-18, LiChroprep RP-8 or RP-18 (5, 10, 25–40 micron silica) from Merck & Co., Inc.; $\mu$-Bondapak-phenyl,—C-18,—CN (10 micron silica) from Waters, Inc.; and Particil-10-ODS (C-18 on 18 micron silica) from Whatman, Inc. The microparticulate silica has a particle size of about 10–40 microns with a particle size in the range of 10–20 microns being preferred. The solvent systems used for these separations are typically polar gradient elution systems with solvent polarity decreasing with time. The solvent systems are generally composed of two or three solvents with a two solvent system being preferred. The two solvent system can contain one or two polar solvents with one polar solvent being preferred.

The flow cell is of the type commercially available and is preferably of a size about 2 mm $\times$ 8 mm. The cell is packed with a non-polar packing material by methods known in the art. The non-polar packing material may be the same as or different from the non-polar column packing material used to separate mixtures of the dansyl derivatives. However, in the case where the packing materials are different, the retention of the flow cell packing must be between $\frac{1}{3}$ and 3 times that of the analytical column to prevent separations in the flow cell. The flow cell packing materials are microparticulate silica bonded to, for example, hydrocarbons of carbon chain length 2–22, phenyl, diphenyl, phenylethyl, or alkylcyano. These packing materials are available commercially as chromatography column packing materials from, for example, Merck, Whatman or Waters (see the column packings listed above). A hydrocarbon of carbon chain length 16–20 is preferred. The microparticulate silica has a particle size in the range of 10–40 microns with a particle size of 10–20 microns being preferred.

Dansylation of active hydrogen compounds by reaction with dansyl chloride is known in the art. Examples of active hydrogen compounds which are particularly illustrative of the present invention are phenols, amines, and amino acids. The preferred amino acids are histidine, lysine and tyrosine.

Detection of dansyl derivatives is typically accomplished using fluorescence. It is known in the art that the fluorescence intensity of dansyl derivatives varies with solvent polarity. For example, dansylethylamine shows a fluorescence intensity of 100 in methanol at a fluorescence maxima of 520 nanometers while in a benzene solvent the intensity is 165 at a fluorescence maxima of 483 nanometers; dansylphenol shows a fluorescence intensity of 10 in methanol at 540 nanometers and a fluorescence intensity of 168 in benzene at 508 nanometers; and dansyltyramine has a fluorescence of 58 in methanol at 525 nanometers and a fluorescence of 232 in benzene at 507 nanometers. The enhancement effects seen in the present invention are similar to the effects illustrated here. If a gradient elution solvent system going from polar to non-polar is used to separate a mixture of dansyl derivatives, the fluorescence for those compounds eluting in a polar solvent will be low while the fluorescence intensity will be higher for those compounds eluting in more non-polar solvents. Quantitation will thus be difficult if the fluorescence intensity varies during the chromatographic run, and larger sample quantities will be required if fluorescence is detected in a polar environment.

In accordance with the present invention, the polar dansyl derivative-containing eluant from the liquid chromatography column is passed through a flow cell packed with the non-polar packing material. In the packed flow cell the environment of the dansyl derivative is changed from polar to non-polar without changing the solvent and a dynamic equilibrium of the dansyl derivative is established between the polar solvent and the non-polar cell packing material. The fluorescence of the dansyl derivative is determined in the non-polar environment using electromagnetic radiation of the appropriate wavelength, and after detection the dansyl derivative is passed out of the packed flow cell in the polar solvent in which the derivative entered the flow cell.

The fluorescence maximum used to irradiate the dansyl derivative is that wavelength known in the literature to be the fluorescence maximum in a non-polar environment for the dansyl derivative of interest. In the present invention, the fluorescence maximum for dansyl derivatives of amino acids in non-polar solvents is about 485 nanometers.

In addition to enhancing the fluorescence of dansyl derivatives of active hydrogen compounds which can be separated in a non-polar liquid chromatography column using a polar solvent system, this method also applies to those cases in which a dansyl derivative of an active hydrogen compound cannot be separated from an impurity or contaminant and the fluorescence of the impurity or contaminant is quenched in a non-polar environment. In this case the polar eluant containing a mixture of a dansyl derivative and an impurity or contaminant is passed through a flow cell packed with a non-polar packing material as is described above. The flow cell is irradiated with the appropriate wavelength of electromagnetic radiation and the fluorescence of the dansyl derivative is detected as described above.

A specific example of the present invention is set forth below. This example is merely illustrative and is not in any way to be interpreted as limiting the scope of this invention.

EXAMPLE

A mixture of dansyl histidine, E-dansyl lysine, and O-dansyl tyrosine is separated on a reverse phase column of 10 micron microparticulate silica to which is chemically bonded a long chain hydrocarbon silicone of carbon length 18 (e.g., LiChrosorb RP-18 from Merck & Co., Inc.) using a gradient elution system of A=0.05 M $KH_2PO_4$, pH 2.1; and B=acetonitrile; 5 to 70% B in 25 minutes and a flow rate of 1 ml/minute. The preparation of both the column packing material and the HPLC column are known in the art.

The eluant from the HPLC column is flowed into a flow cell packed with 10 micron microparticulate silica to which is chemically bonded a long chain hydrocarbon 18-carbon silicone of carbon length 18 (e.g., LiChrosorb RP-18 from Merck & Co., Inc.). The flow cell is 2 mm×8 mm and the flow rate is 1 ml/minute. The flow cell is packed according to procedures known in the art.

The packed flow cell is irradiated with a wavelength of light which is the maximum for the compounds in a non-polar environment or about 485 nanometers for the dansyl amino acids of this example and the fluorescence is detected using a commercially available fluorescence detector such as Fluorichrom.

The danysl derivative is flowed out of the packed cell in the polar eluant in which the dansyl derivative entered the packed cell.

Further information on the method of this example is given in the table below:

TABLE

| Dansyl Compound | Elution Time, Min. | Fluorescence Intensity | |
|---|---|---|---|
| | | Empty Cell (Comparison - Polar Environ.) | Packed Cell According to the Invention (Non-Polar Environ.) |
| Histidine | 7.8 | 0.4 | 9.3 |
| Lysine | 14.9 | 4.0 | 76.8 |
| Tyrosine | 28.6 | 1.2 | 6.7 |

Also contained in this Table is data for experimentation that was identical to that carried out above except that the flow cell was empty.

We claim:

1. A method for enhancing the fluorescence detectability of dansyl derivatives of active hydrogen compounds, which are ideally separated by liquid chromatography using a non-polar column packing material and a polar solvent system but whose fluorescence efficiency is diminished by the presence of polar solvents, said method comprising the steps of
    (a) passing a polar eluant bearing at least one of said dansyl derivatives through a flow cell packed with a non-polar packing material whereby there is caused a dynamic equilibrium of at least one of said dansyl derivatives between the said polar solvent system and the said non-polar cell packing material; wherein said eluant is eluted from a liquid chromatography column packed with an appropriate non-polar packing material using a polar solvent system;
    (b) irradiating said flow cell with electromagnetic radiation of a frequency that causes said dansyl derivative to fluoresce in the non-polar environment; and
    (c) detecting the emitted fluorescence; whereby the environment of at least one of said dansyl derivatives is changed to a non-polar environment without changing the solvent.

2. The method of claim 1 wherein said non-polar column packing material is a microparticulate silica to which is chemically bonded a member of a group comprising a hydrocarbon of carbon chain length 2-22, phenyl, diphenyl, phenylethyl and alkylcyano.

3. The method of claim 2 wherein said hydrocarbon has a carbon chain length of 16-20.

4. The method of claim 1 wherein the polar solvent system consists of a polar solvent and a non-polar solvent.

5. The method of claim 1 wherein said non-polar cell packing material is microparticulate silica to which is chemically bonded a member of a group comprising a hydrocarbon of carbon chain length 2-22 phenyl, diphenyl, phenylethyl, and alkylcyano.

6. The method of claim 5 wherein said hydrocarbon has a chain length of 16-20.

7. The method of claim 1 wherein said flow cell packing material is the same as the said column packing material.

8. The method of claim 1 wherein said flow cell packing material is different from said column packing material and said flow cell packing material has a retention ⅓ to 3 times that of said column packing material to prevent separation on the said flow cell packing material.

9. The method of claim 1 wherein said dansyl derivatives are separated on an HPLC column.

10. The method of claim 1 wherein the said non-polar column packing material is microparticulate silica to which is chemically bonded a long chain hydrocarbon silicone of carbon length 18.

11. The method of claim 1 wherein the said polar solvent system is a mixture of about 0.05 M potassium orthophosphate, about pH 2.1, and acetonitrile; wherein the composition of this solvent system changes from about 5 to 70% acetonitrile in about 25 minutes.

12. The method of claim 1 wherein said dansyl derivatives are dansyl derivatives of amino acids which are members of a group comprising dansyl histidine, E-dansyl lysine, and O-dansyl tyrosine.

13. The method of claim 1 wherein said flow cell packing material is microparticulate silica to which is chemically bonded a long chain hydrocarbon silicone of carbon chain length 18.

14. The method of claim 1 wherein the said packed flow cell is irradiated with electromagnetic radiation of about 485 nanometers.

15. A method for enhancing the fluorescence detectability of dansyl derivatives of active hydrogen compounds, which cannot be separated from impurities or contaminants by liquid chromatography using a non-polar column packing material and a polar solvent system, but the fluorescence efficiency of said dansyl derivative is diminished by the presence of polar solvents and the fluorescence efficiency of said impurity or contaminant is diminished by the presence of non-polar solvents, said method comprising the steps of:
    (a) passing a polar eluant bearing at least one of said dansyl derivatives and the said impurity or contaminant through a flow cell packed with a non-polar packing material whereby there is caused a dynamic equilibrium of at least one of said dansyl derivatives and the said impurity or contaminant between the said polar solvent system and the said non-polar cell packing material; wherein said eluant is eluted from a liquid chromatography column packed with an appropriate non-polar packing material using a polar solvent system;

(b) irradiating said flow cell with electromagnetic radiation of a frequency that causes said dansyl derivative to fluoresce in the non-polar environment and causes said impurity or contaminant fluorescence to be diminished in the non-polar environment; and (c) detecting the emitted fluorescence;

whereby the environment of at least one of said dansyl derivatives is changed to a non-polar environment without changing the solvent.

16. The method of claim 15 wherein said non-polar column packing material is a microparticulate silica to which is chemically bonded a member of a group comprising a hydrocarbon of carbon chain length 2–22, phenyl, diphenyl, phenylethyl and alkylcyano.

17. The method of claim 16 wherein said hydrocarbon has a carbon chain length of 16–20.

18. The method of claim 15 wherein the polar solvent system consists of a polar solvent and a non-polar solvent.

19. The method of claim 15 wherein said non-polar cell packing material is microparticulate silica to which is chemically bonded a member of a group comprising a hydrocarbon of carbon chain length 2–22, phenyl, diphenyl, phenylethyl, and alkylcyano.

20. The method of claim 19 wherein said hydrocarbon has a carbon chain length of 16–20.

21. The method of claim 15 in which said flow cell packing material is the same as the said column packing material.

22. The method of claim 15 in which said flow cell packing material is different from said column packing material and said flow cell packing material has a retention $\frac{1}{3}$ to 3 times that of said column packing material to prevent separation on the said flow cell packing material.

23. The method of claim 15 wherein said dansyl derivatives and said impurities or contaminants are separated as a mixture on an HPLC column.

24. The method of claim 15 wherein the said non-polar column packing material is microparticulate silica to which is chemically bonded a long chain hydrocarbon silicone of carbon length 18.

25. The method of claim 15 wherein the said polar solvent system is a mixture of about 0.05 M potassium orthophosphate, about pH 2.1, and acetonitrile; wherein the composition of this solvent system changes from about 5 to 70% acetonitrile in about 25 minutes.

26. The method of claim 15 wherein said dansyl derivatives are dansyl derivatives of amino acids which are members of a group comprising dansyl histidine, E-dansyl lysine, and O-dansyl tyrosine.

27. The method of claim 15 wherein said flow cell packing material is microparticulate silica to which is chemically bonded a long chain hydrocarbon silicone of carbon chain length 18.

28. The method of claim 15 wherein the said packed flow cell is irradiated with electromagnetic radiation of about 485 nanometers.

* * * * *